United States Patent [19]

Imfeld et al.

[11] Patent Number: 4,565,869
[45] Date of Patent: Jan. 21, 1986

[54] DICARBAMATES

[75] Inventors: Marquard Imfeld, Oberwil; Henri Ramuz, Birsfelden; Peter Vogt, Aesch, all of Switzerland; Jean-Claude Muller, Morsang-sur-Orge, France

[73] Assignee: Hoffmann-La Roche Inc., Nutley, N.J.

[21] Appl. No.: 472,696

[22] Filed: Mar. 7, 1983

[30] Foreign Application Priority Data

Mar. 16, 1982 [CH] Switzerland ............... 1639/82

[51] Int. Cl.⁴ ..................................... C07D 239/48
[52] U.S. Cl. ................................ 544/323; 544/320
[58] Field of Search ................... 544/319, 323, 320

[56] References Cited

U.S. PATENT DOCUMENTS 4,175,189  11/1979  Muller et al. .................. 544/323

OTHER PUBLICATIONS

Sandler et al., Organic Functional Group Preparations, vol. 11, pp. 244–245 (1971).

Primary Examiner—Robert Gerstl
Attorney, Agent, or Firm—Jon S. Saxe; George M. Gould; Patricia A. Coburn

[57] ABSTRACT

Novel pyrimidinedicarbamates of the formula

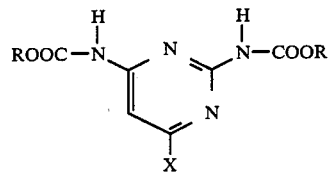

wherein R is lower alkyl or (lower alkyloxy)-(lower alkyl) and
X is a leaving group, can be manufactured by carbamoylating the corresponding free diamines. They are valuable intermediates and can be used, for example, for the manufacture of corresponding oxadiazolopyrimidines of the formula

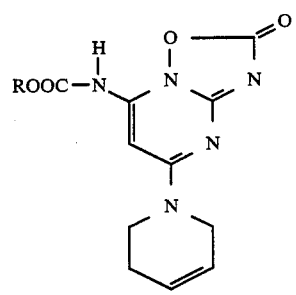

and pharmaceutically acceptable salts thereof. The latter have valuable long-lasting vasodilating and/or bloodpressure lowering properties and are accordingly suitable especially for the treatment of vascular-conditioned hypertensions or as vasodilators in the case of peripheral blood supply disorders.

4 Claims, No Drawings

DICARBAMATES

The present invention is concerned with novel dicarbamate compounds of the formula

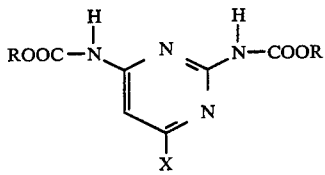

wherein R is a lower alkyl or a (lower alkyloxy)-(lower alkyl) and
X is a leaving group.

These compounds are valuable intermediates. They can be used, for example, for the manufacture of oxadiazolopyrimidines of the general formula

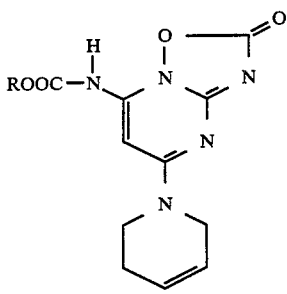

wherein R is as described above,
and pharmaceutically acceptable salts thereof, which have long-lasting valuable vasodilating and/or blood pressure-lowering properties and which accordingly can be used for the treatment of vascular-conditioned hypertensions or also as vasodilators in the case of peripheral blood supply disorders.

The terms "lower alkyl" or "lower alkyl group" are intended to denote saturated hydrocarbon groups containing at most 8, preferably at most 4, carbon atoms, which can be straight-chain or branched-chain such as, for example, methyl, ethyl, n-propyl, isopropyl, n-butyl, isobutyl, t-butyl and the like. The term "lower alkyloxy" denotes a lower alkyl group as defined earlier bonded via an oxygen atom. The term "(lower alkyloxy)-(lower alkyl)" denotes an ether group formed by the union of a lower alkyloxy and a lower alkyl.

The term "leaving group" embraces primarily halogen atoms such as chlorine, bromine and iodine and sulfonic acid groups such as methanesulfonyloxy, p-toluenesulfonyloxy, p-bromobenzenesulfonyloxy and benzenesulfonyloxy.

R preferably is a lower alkyl, with methyl being especially preferred. X preferably is chlorine.

Dimethyl 6-chloro-3,4-pyrimidinedicarbamate is a particularly preferred compound of formula I.

The compounds of formula I can be manufactured in accordance with the invention by reacting a 2,4-diaminopyrimidine of the formula

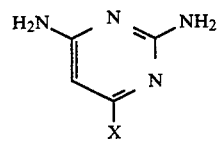

wherein X is a leaving group as hereinbefore described, in the presence of a base, with a compound of the formula $$Z-\overset{O}{\underset{\|}{C}}-OR \qquad IV$$

wherein Z is a halogen atom, an R—O—group, or a 1-imidazolyl group and wherein R is as hereinbefore described.

The reaction conditions to be used depend on the nature of the compound of formula IV used.

For example, if a compound of formula IV in which Z is a halogen is used, then there primarily come into consideration chloroformic acid esters and the reaction is conveniently carried out in an organic solvent or solvent mixture which is inert under the reaction conditions. Suitable solvents are chlorinated hydrocarbons such as methlene chloride or chloroform, ethers such as diethyl ether, tetrahydrofuran or dioxane, dimethylformamide and the like or mixtures thereof. The reaction can also be carried out in a water-containing solvent or in the presence of water in a two-phase system such as, for example, methylene chloride/water. As bases there come into consideration especially tertiary amines such as triethylamine, ethyldiisopropylamine, trimethylamine and pyridine, alkali metal hydroxides such as sodium hydroxide and potassium hydroxide, alkali metal alkoxides such as potassium t-butylate or alkali metal hydrides such as sodium hydride. If the reaction is carried out in the presence of a liquid base, then this can also be used as the solvent. The reaction is conveniently carried out at temperatures between about −10° C. and room temperature, preferably between about 0° C. and 10° C.

If a compound of formula IV in which Z is 1-imidazolyl (i.e. an imidazolide) is used, then the reaction is conveniently carried out in an inert organic solvent, with ethers such as tetrahydrofuran, dioxane, diethyl ether or the like, dimethylformamide, dimethyl sulfoxide or the like being especially suitable. As bases there come into consideration especially alkali metal hydrides such as sodium hydride, alkali metal alkoxides such as sodium methylate, potassium t-butylate and the like, alkali metal hydroxides such as sodium hydroxide and potassium hydroxide and alkali metal carbonates such as potassium carbonate. The reaction is conveniently carried out at a temperature in the range of about 0° C. to the boiling point of the reaction mixture.

In a preferred embodiment, however, there are used compounds of formula IV in which Z is an R—O—group (i.e., the compound is a corresponding carbonate). This reaction is carried out in an organic solvent or solvent mixture which is inert under the reaction conditions, with ethers such as tetrahydrofuran, dioxane, diethyl ether or the like, dimethylformamide, dimethyl sulfoxide, excess carbonate of formula IV or mixtures thereof being especially suitable. The use of excess carbonate of formula IV as the solvent is especially preferred. As bases there come into consideration especially sodium hydride and the alkali metal alkoxides or alkyloxyalkoxides corresponding to the carbonate of formula IV used such as, for example, sodium methylate. Based upon the compound of formula III there are preferably used at least 2 to about 4 equivalents of base. The reaction can be carried out in a temperature range of from about room temperature to the boiling point of the reaction mixture.

As mentioned earlier, the compounds of formula I are valuable intermediates for the manufacture of pharmacologically active oxadiazolopyrimidines of formula II. The conversion in accordance with the invention of compounds of formula I into oxadiazolopyrimidines of formula II is illustrated in more detail by the following Formula Scheme in which R and X are as hereinbefore described.

xylene and the like or mixtures thereof especially coming into consideration. In place of an inert solvent there can also be used excess 1,3,5,6-tetrahydropyridine. The reaction is preferably carried out under an inert gas atmosphere, preferably under argon or nitrogen, with the temperature conveniently lying between about 0° C. and 50° C.

By cyclizing a compound of formula VI there is finally obtained an oxadiazolopyrimidine of formula II. This likewise known reaction is carried out by heating a compound of formula VI to a temperature between about 50° C. and 200° C., preferably between about 100° C. and 150° C. The reaction can be carried out in the absence or presence of a solvent or solvent mixture. If the reaction is carried out in a solvent or solvent mixture, then there come into consideration especially aromatic hydrocarbons such as benzene, toluene or xylene, Formula Scheme

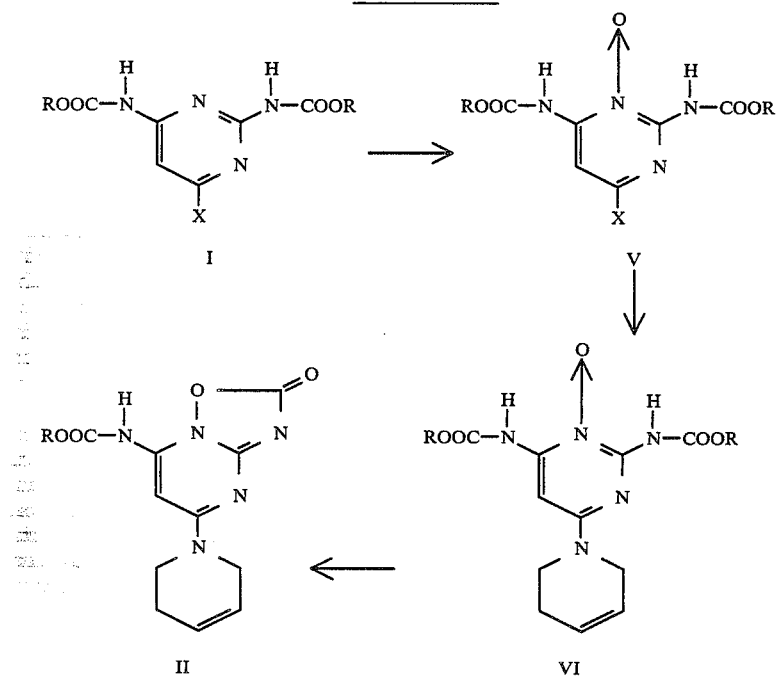

The N-oxidation of a compound of formula I to give a compound for formula V can be carried out with an organic peracid. Suitable organic peracids for this purpose are, for example, peracetic acid, monoperphthalic acid, m-chloroperbenzoic acid, pertrifluoroacetic acid, monopermaleic acid, dichloromonopermaleic acid, p-nitroperbenzoic acid and perbenzoic acid. The oxidation is conveniently carried out in an organic solvent which is inert under the reaction conditions; for example, a halogenated hydrocarbon such as methylene chloride, 1,2-dichloroethane, chloroform or the like, an ester such as ethyl acetate, isopropyl acetate or the like, acetonitrile or the like. The reaction is preferably carried out at a temperature in the range of from about room temperature to the boiling point of the reaction mixture.

By reacting a compound of formula V with 1,2,5,6-tetrahydropyridine there is obtained a compound of formula VI. This known reaction is carried out in an inert organic solvent or solvent mixture, with chlorinated hydrocarbons such as methylene chloride or chloroform, aromatic hydrocarbons such as toluene or chlorinated hydrocarbons such as chloroform, alcohols such as butanol or isobutanol, ethers such as dibutyl ether, dioxane, diethylene glycol dimethyl ether, dimethylformamide, dimethyl sulfoxide and the like or mixtures thereof.

The oxadiazolopyrimidines of formula II can be converted into pharmaceutically acceptable salts with inorganic or organic bases in a known manner.

The compounds of formula III used as starting materials and the compounds of formulae II, V and VI are known.

Objects of the present invention are the compounds of formula I per se, a process for their manufacture, a process for the manufacture of compounds of formula V from compounds of formula I, the use of this process in the manufacture of oxadiazolpyrimidines of formula II as well as the use of compounds of formula I in the manufacture of oxadiazolopyrimidines of formula II.

The following examples illustrate the present invention in more detail. All temperatures are in degrees centigrade.

EXAMPLE 1

A mixture of 144.6 g (1 mol) of 2,4-diamino-6-chloropyrimidine and 2170 ml of dimethyl carbonate is heated to about 80° under nitrogen and while stirring and then treated dropwise over a period of 30 minutes with 373 ml (2 mol) of a 30 percent solution of sodium methylate in methanol, a white suspension resulting. The mixture is thereafter stirred at about 70° for a further hour, poured into a mixture of 3 kg of ice and 1 l of water, treated with 1440 g of sodium chloride and stirred, while cold, for 1 hour. The white precipitation is subsequently separated by suction filtration under a slight vacuum, and the residue is then washed until neutral using three 500 ml portions of ice-cold water. After drying, there is obtained dimethyl 6-chloro-2,4-pyrimidinedicarbamate as a white solid of melting point 156°–158°.

EXAMPLE 2

A mixture of 18.7 g (0.385 mol) of 70 percent hydrogen peroxide and 400 ml of methylene chloride, stirred under argon and cooled to about 0°, is treated with 49.0 g (0.5 mol) of maleic acid anhydride. The mixture is stirred at 0° for 5 minutes and subsequently treated dropwise over a period of 15 minutes with a solution of 13.0 g (0.05 mol) of dimethyl 6-chloro-2,4-pyrimidinedicarbamate in 1500 ml of methylene chloride in such a manner that the temperature does not exceed 2°. The cooling bath is removed, the mixture is stirred for a further 15.5 hours, cooled to 3° and filtered. The white solid residue is subsequently washed with 400 ml of semi-saturated ice-cold sodium carbonate solution and then with 100 ml of ice-water. The material obtained is taken up in 150 ml of benzene and evaporated. This procedure is repeated once more and then the residue is dried at 60° under vacuum. There is obtained dimethyl 6-chloro-2,4-pyrimidinedicarbamate 3-oxide as a white solid of melting point 224°–225°.

The dimethyl 6-chloro-2,4-pyrimidinedicarbamate 3-oxide thus produced is converted in a known manner as described hereinafter into the corresponding oxadiazolopyrimidine of formula II:

(a) A suspension of 5.0 g (0.018 mol) of dimethyl 6-chloro-2,4-pyrimidinedicarbamate 3-oxide in 100 ml of methylene chloride is treated with 10 ml (0.22 mol) of 1,2,5,6-tetrahydropyridine and the mixture is heated to boiling for 3 hours under an argon atmosphere and while stirring. The mixture is evaporated under vacuum, the residue is taken up in chloroform, the organic phase is washed with water, dried over sodium sulphate and evaporated under vacuum. By recrystallization of the residue from methylene chloride/ethyl acetate there is obtained pure dimethyl 6-[3,6-dihydro-1(2H)-pyridyl]-2,4-pyrimidinedicarbamate 3-oxide in the form of white crystals of melting point 206°.

(b) 32.3 g (0.1 mol) of dimethyl 6-[3,6-dihydro-1(2H)-pyridyl]-2,4-pyrimidinedicarbamate 3-oxide are stirred at room temperature for 3 hours in a mixture of methylene chloride and 3 percent sodium hydroxide solution. The two phases are separated and the aqueous phase is made acid, there being obtained methyl 5-[3,6-dihydro-1(2H)-pyridyl]-2-oxo-2H-[1,2,4]oxadiazolo[2,3-a]pyrimidine-7-carbamate of melting point 210°–212°.

EXAMPLE 3

A solution of 2.7 g (0.041 mol) of imidazole in 50 ml of dry tetrahydrofuran is treated at 0° C. with 1.8 g (0.041 mol) of 55 to 60 percent sodium hydride. After the hydrogen formation has finished, 3.8 g (0.041 mol) of methyl chloroformate in 20 ml of dry tetrahydrofuran are added dropwise at 0° C., whereupon the suspension obtained is treated dropwise at 0° with a solution of 2.9 g (0.021 mol) of 6-chloro-2,4-diaminopyrimidine and 4.5 g (0.041 mol) of potassium t-butylate in 30 ml of dry dimethylformamide. The mixture is stirred at 0° for 1 hour and then at 50° for 3 hours, whereupon 3 ml of methanol are added thereto and the solvent is evaporated to the largest extent possible. The residue is poured into ice-cold water, adjusted with 1N hydrochloric acid to pH 2 and extracted with methylene chloride and a small amount of methanol. After drying the organic extract over magnesium sulphate and evaporation under vacuum, the residue is recrystallized from ethyl acetate, there being obtained pure dimethyl 6-chloro-2,4-pyrimidinedicarbamate.

EXAMPLE 4

A solution of 21.6 g (0.15 mol) of 6-chloro-2,4-diaminopyrimidine in 100 ml of dry tetrahydrofuran is treated with 50 g (0.45 mol) of potassium t-butylate while stirring, whereupon the yellow suspension obtained is cooled to 0° and treated with a solution of 42.5 g (0.45 mol) of methyl chloroformate in 60 ml of dry tetrahydrofuran. The mixture is stirred at 0° for 1 hour and at room temperature overnight, treated with water while cooling with ice, adjusted with 3N sodium hydroxide solution to pH 10 and extracted with ethyl acetate. The organic phase is washed with 3N hydrochloric acid while cooling with ice, dried over magnesium sulphate and evaporated. The residue obtained is chromatographed on silica gel while eluting with toluene/ethyl acetate (7:3), there being obtained pure dimethyl 6-chloro-2,4-pyrimidinedicarbamate.

EXAMPLE 5

A solution of 7.25 g (50 mmol) of 6-chloro-2,4-diaminopyrimidine in 100 ml of dimethylformamide and 20 ml of triethylamine is cooled to 0° and treated dropwise with 10 ml of ethyl chloroformate. The mixture is stirred at room temperature for 70 hours, the precipitated material is filtered off under suction, the filtrate is evaporated and the residue is taken up in methylene chloride. The organic phase is washed with 1N hydrochloric acid, dried over magnesium sulphate and evaporated under vacuum. The crude product obtained is chromatographed on silica gel, there being obtained pure diethyl 6-chloro-2,4-pyrimidinedicarbamate of melting point 153°–154°.

What is claimed is:

1. Dicarbamates of the formula

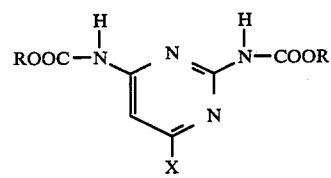

wherein R represents a member of the group consisting of lower alkyl and (lower alkyloxy)-(lower alkyl), and X represents a halogen atom or a sulfonic acid group.

2. Compounds according to claim 1, wherein R is a lower alkyl.

3. Compounds according to claim 1 or claim 2, wherein X is chlorine.

4. Dimethyl 6-chloro-2,4-pyrimidinedicarbamate.

* * * * *